(12) United States Patent
Kobayashi

(10) Patent No.: US 9,193,975 B2
(45) Date of Patent: Nov. 24, 2015

(54) FREE BRANCHING POINSETTIA

(75) Inventor: Ruth Kobayashi, Carlsbad, CA (US)

(73) Assignee: DUMMEN GROUP B.V., De Lier (NL)

( * ) Notice: Subject to any disclaimer, the term of this patent is extended or adjusted under 35 U.S.C. 154(b) by 289 days.

(21) Appl. No.: 13/528,023

(22) Filed: Jun. 20, 2012

(65) Prior Publication Data

US 2013/0086709 A1    Apr. 4, 2013

Related U.S. Application Data

(60) Provisional application No. 61/499,308, filed on Jun. 21, 2011.

(51) Int. Cl.
*A01H 5/04* (2006.01)
*C12N 15/82* (2006.01)

(52) U.S. Cl.
CPC .............. *C12N 15/8241* (2013.01); *A01H 5/04* (2013.01); *C12N 15/8262* (2013.01)

(58) Field of Classification Search
CPC .................................................. A01H 5/0244
USPC ......................................................... 800/323
See application file for complete search history.

(56) References Cited

U.S. PATENT DOCUMENTS

| | | | |
|---|---|---|---|
| 4,724,276 A | 2/1988 | Ecke | |
| PP8,833 P | 7/1994 | Fruehwirth | |
| PP10,253 P | * 2/1998 | Hrebeniuk | |
| 2007/0056066 P1 | * 3/2007 | Anatriello | |
| 2007/0067876 A1 | 3/2007 | Smith et al. | |
| 2007/0083948 A1 | 4/2007 | McAvoy et al. | |
| 2010/0281568 A1 | 11/2010 | Clarke et al. | |

FOREIGN PATENT DOCUMENTS

WO    WO 99/06566    2/1999

OTHER PUBLICATIONS

Casanova, et al., "Influence of *rol* genes in floriculture", *Biotechnology Advances*, 23:3-39, 2005.
Clifford, et al., "Height control of poinsettia using photoselective filters", *HortScience*, 39(2):383-387, 2004.
Lee, et al., "Revised classification scheme of phytoplasmas based on RFLP analyses of 16S rRNA and ribosomal protein gene sequences", *International Journal of Systemic Bacteriology*, 48:1153-1169, 1998.
PCT International Search Report and Written Opinion issued in International Application No. PCT/US2012/043235, mailed Oct. 16, 2012,.

* cited by examiner

*Primary Examiner* — Jared Shapiro
(74) *Attorney, Agent, or Firm* — Parker Highlander PLLC

(57) ABSTRACT

Free branching poinsettia plants are provided which comprise a heritable lateral branching trait. In certain aspects, poinsettia plants comprising a lateral branching trait are not pinched, are not grafted and/or are free of phytoplasma infection. Methods for growth and breeding such free branching poinsettias are also provided.

9 Claims, 10 Drawing Sheets

FREE BRANCHING POINSETTIA

This application claims priority to U.S. Application No. 61/499,308 filed on Jun. 21, 2011, the entire disclosure of which is specifically incorporated herein by reference in its entirety without disclaimer

BACKGROUND OF THE INVENTION

1. Field of the Invention

The present embodiments provided herein relate generally to horticultural, plant breeding and plant genetics.

2. Description of Related Art

Ornamental plants such as begonias, geraniums, impatiens and poinsettias comprise a large and profitable market both in the U.S. and abroad. The poinsettia (*Euphorbia pulcherrima* Willd.), for example, is a member of the family Euphorbiaceae which is very popular as a live ornamental decoration. The highly prized blooms of these plants, known as bracts, are not true flowers, but rather modified leaves that form large flower-like arrays. Popular ornamental varieties produce bracts in a variety of brilliant colors such as red, orange, white, yellow and pink.

Production of quality ornamental poinsettias can be difficult and labor intensive. In the wild, plants produce a single bloom from a tall (up to ten foot) vertical stem. On the other hand, ornamental poinsettias preferably have a mounded bushy habit with multiple lateral branches. To produce such plants, the growth tip of the poinsettia is mechanically removed during the vegetative growth phase by a process known as pinching. Such pinching stimulates lateral branching and can be used to control the size of the resulting plant. Alternatively or additionally, lateral branching can be stimulated by exposure of the plants to a branching agent, such as the poinsettia, branch-inducing phytoplasma (Lee et al. 1998). For instance, plants can be inoculated with phytoplasma by grafting of phytoplasma-infected plant tissues. All of the above methods, however, require substantial labor and therefore result in increased production cost.

SUMMARY OF THE INVENTION

In a first embodiment a poinsettia plant is provided comprising a lateral branching trait that is transmitted to at least a portion of progeny plants when the plant is crossed with a second plant that does not comprise a lateral branching trait. For example, the lateral branching trait can be transmitted to at least about 30% (e.g., about 30%, 40%, 50%, 60%, 70%, 80%, 90%, or 95% to 99% or more) of progeny plants when crossed with the second plant. A plant according to the embodiment, in some aspects, can be further defined as a plant that has not been pinched, grafted or treated with a branching agent. For example, the plant can be free of phytoplasma infection. In certain aspects, the lateral branching trait is defined as a genetic trait.

In a further embodiment there is provided a poinsettia plant comprising a lateral branching trait wherein the plant has not been pinched and is free of phytoplasma infection. For example, in certain aspects, a plant according to the embodiment has not been treated with a branching agent. In some cases, such a plant can further be defined as a plant that can transmit a lateral branching trait to at least a portion of progeny plants when crossed with a second plant that does not comprise a lateral branching trait. For example, the lateral branching trait can be transmitted to about 10%-99%, 20%-99% or 30%-99% of progeny plants (e.g., about 10%, 20%, 30%, 40%, 50%, 60%, 70%, 80%, 90%, or 95% to 99% or more of progeny plants) when the plant is crossed with the second plant.

In certain embodiments, a poinsettia plant comprising a lateral branching trait comprises a plurality of lateral branches such at least about 3 lateral branches. For instance, such a plant can comprise 5, 10, 15, 20, 25 or more branches (e.g., from about 3, 4, 5, 6, 7 branches to about 20, 25 or 30 branches). In some aspects, a plant may also be defined by the proportion of nodes that develop a lateral branch. For instance, at least about 30% of the nodes of the plant can develop a branch. In further aspects, at least about 40%, 50%, 60%, 70%, 80%, 90%, or 95% of nodes develop a lateral branch.

In still further aspects, a plant according to the embodiments is defined as comprising at least one elite trait in addition to a lateral branching trait. For example, the elite trait can be any horticultural important trait including, but not limited to, short stature, upright growth, strong branches, large blooms, large bracts, large inflorescences, vigorous growth, disease resistance, insect resistance, increased longevity, midseason flowering, increased period of flowering, uniform plant habit, a desired leaf color (e.g., green, medium green, dark green or variegated green) or morphology, flower bracts with desirable colors or brilliant bract color. For example, a poinsettia plant according to the embodiments can comprise bracts that are red (e.g., dark red or rose), orange, purple, salmon, pink, cream, yellow, white, pale green, marbled or a combination thereof. In yet further aspects a plant according to the embodiments comprise a transgene, such as a transgene conferring herbicide tolerance or insect or disease resistance. Methods for producing transgenic poinsettia plants are described, for example, in U.S. Patent Publ. Nos. 20100281568 and 20070067876, incorporated herein by reference.

In further embodiments, plant parts of a poinsettia plant according to the embodiments are included as part of the invention. For example, the plant part can be a seed, a stalk, a bract, a bud, a leaf, a root or a cell. In certain aspects, a plant part is a part which can be regenerated into a whole plant (e.g., a whole plant comprising a lateral branching trait). Thus, in some aspects, the plant part is a living plant part.

In another embodiment of the invention, a tissue culture of regenerable cells of a poinsettia plant comprising a lateral branching trait is provided. The tissue culture will preferably be capable of regenerating plants capable of expressing a lateral branching trait. The regenerable cells in such tissue cultures can, in certain aspects, be derived from embryos, meristematic cells, pollen, leaves, anthers, roots, root tips, bracts and seeds or from callus or protoplasts derived from those tissues. The present invention further provides poinsettia plants regenerated from the tissue cultures of the invention, the plants comprising a lateral branching trait according to the invention.

In still a further embodiment there is provided a method of producing a free branching poinsettia plant comprising obtaining a seed or cutting of a plant comprising a lateral branching trait according to the embodiments and allowing a plant to grow there from. Thus, in certain aspects, a method may be defined a method for producing a free branching poinsettia plant without pinching, grafting and/or infecting the plant with a phytoplasma.

In still a further embodiment there is provided a poinsettia plant, which produces progeny plants comprising a lateral branching trait when said plant is crossed with a second poinsettia plant. In certain aspects, a poinsettia plant according to this embodiment may not, itself, express a lateral branching trait. Nonetheless, the plant is able to produce progeny plants wherein at least about 10%, 20%, 30%, 40% or more (e.g., about 30%-99%) of the progeny express a lateral branching trait. Accordingly, in certain aspects, a method of producing a free branching poinsettia plant is provided comprising crossing such a poinsettia plant with a second poinsettia plant and selecting a progeny plant comprising a lateral branching trait.

In still yet a further embodiment there is provided a method for producing a poinsettia plant comprising (a) crossing a free branching poinsettia plant according to the embodiments with a second plant (e.g., a plant comprising a horticultural desirable trait) and (b) selecting at least a first progeny plant. For example, the method comprises selecting at least a first progeny plant comprising a lateral branching trait. In yet a further aspect, the method comprises selecting at least a first progeny plant for at least a second trait (e.g., a trait from the second parent plant). In such a method the free branching poinsettia plant can be used as either the male or female parent.

In still yet a further embodiment, the invention provides a poinsettia plant comprising an introgression from the poinsettia population deposited as Accession No. NCIMB 41844 wherein said plant comprises a lateral branching trait. For example, such a plant can comprise lateral branching without pinching, grafting and/or phytoplasma infection. In certain aspects, a poinsettia plant comprising a lateral branching trait is defined as comprising a gene region from the poinsettia population deposited as Accession No. NCIMB 41844. Methods for identifying such a gene region by, for example, DNA fingerprinting is provided in U.S. Pat. No. 7,695,901, incorporated herein by reference.

In further development of free-branching poinsettias, populations of seedlings from crosses with free-branching phenotype parents developed through recurrent selection, it was noticed that in certain cross combinations a proportion of the seedling population expressed both primary lateral branch development and optionally secondary lateral branch development without pinching and/or grafting to introduce a branching agent.

In all the embodiments of the invention the lateral branches may be primary, secondary and further branches.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to the drawings in combination with the detailed description of specific embodiments presented herein.

DESCRIPTION OF ILLUSTRATIVE EMBODIMENTS

Ornamental poinsettia plants of the greatest commercial value typically have a bushy mounded habit and produce multiple blooms. However, in the wild poinsettias have a single primary shoot which can reach up to ten feet in height before flowering. Accordingly, poinsettia seedlings are typically pinched during vegetative growth to stimulate lateral branching. Poinsettia plants can also be grafted to other poinsettias containing a branching agent (e.g., a phytoplasma) to stimulate development of lateral branches. However, both pinching and grafting are highly labor intensive and therefore expensive processes.

Figure 1:
FIG. 1: An example of an unpinched poinsettia plant without a lateral branching trait which is in bloom.

Absent pinching and/or infection with phytoplasma, poinsettias do not regularly develop lateral branches until the primary shoot has terminated growth. However, it was noted by the inventors that minimal lateral branching appeared at random in poinsettia populations (i.e., in less than about 1% of plants in a population). In each case the lateral branches developed at less than 25% of nodes late in vegetative growth and were positioned distal to the primary shoot meristem (at more than 7 nodes distant from the meristem). FIG. 1 shows the morphology typical of the minimal branching that was observed in these plants. This minimal level of branching was of no commercial relevance because it was not sufficient to achieve a bushy plant habit at the time of flowering that is needed for commercial cultivars. Nonetheless, despite the presence of minimal branching, tests revealed that the identified plants were free from phytoplasma infection, which was previously thought to be a prerequisite for any such lateral branching.

Figure 6:
FIG. 6: Free branching poinsettia with flowering main shoot and flowering primary and secondary lateral branches, without phytoplasma (exogenous branching agent) and without pinching.

It has now been found that the minimal amount of lateral branching occurring at random can be enhanced by selective breeding of the plants. Plants identified with at least a first lateral branch are selected and crossed with a second poinsettia plant which expresses horticultural elite traits. Again, a small number of the resulting progeny plants display an initial lateral branch. From these progeny, plants are selected that display the greatest amount of branching and largest branches and these plants are crossed with a second plant which likewise displays lateral branching. Additional step(s) of intercross and selection are performed, resulting in progeny plants with increasing levels of branching. In each case, the primary selection criteria are the amount of lateral branching and the size of the lateral branches. By recurrent selection of seedlings for higher percentage of primary and optionally secondary lateral branch development, flowering plants that exhibit a more bush type habit without grafting or pinching can be developed. This is illustrated in FIG. 6.

Figure 2:
FIG. 2: An example of an unpinched and phytoplasma-free poinsettia plant according to the invention comprising a lateral branching trait which is in bloom.
Figure 3:
FIG. 3: Seedling from random cross combination of poinsettia plants without a lateral branching trait. The plant is phytoplasma-free and has not been grafted.
Figure 4:
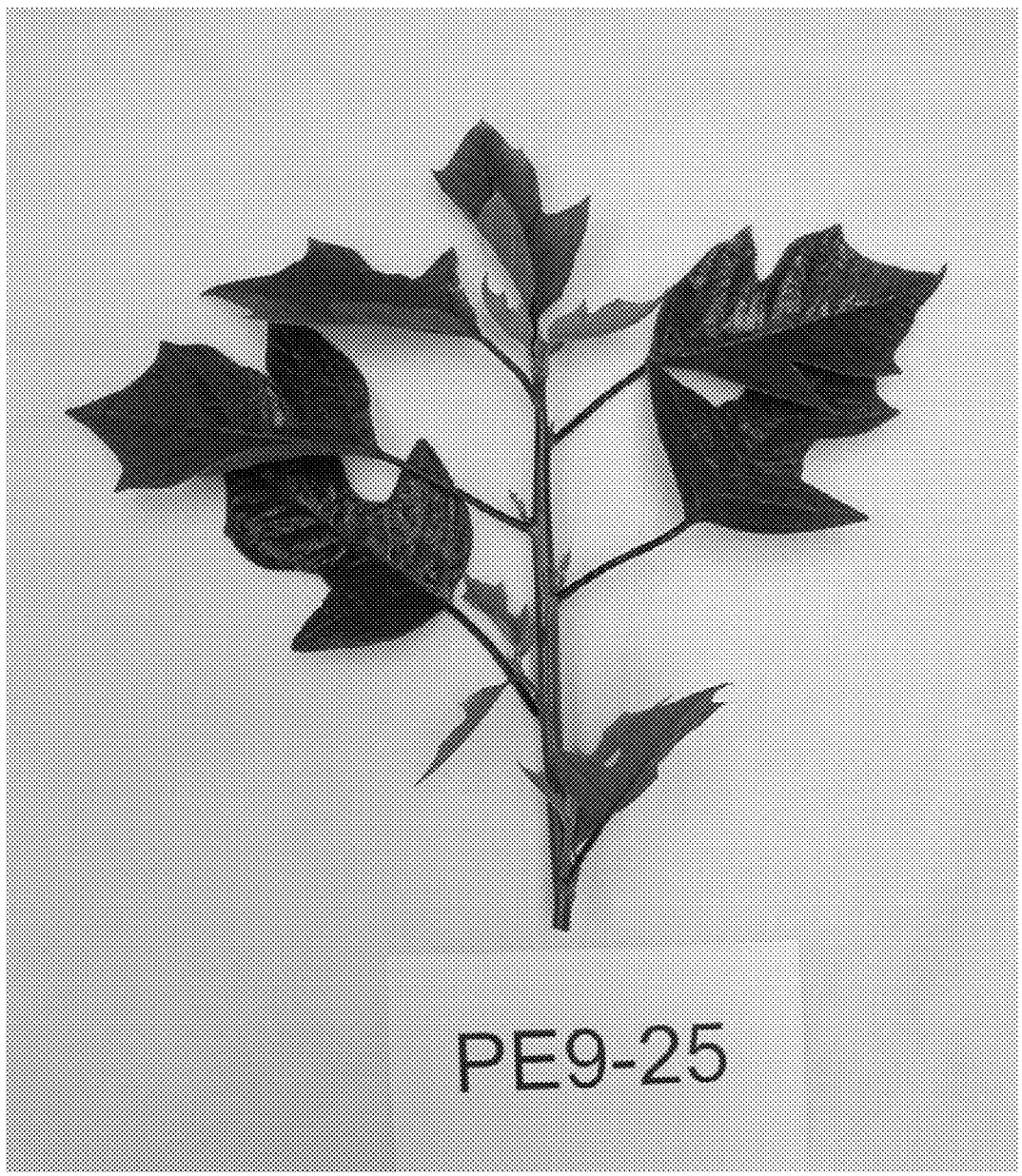
FIG. 4: An example of poinsettia cultivar comprising a lateral branching trait during vegetative growth. The plant is phytoplasma-free and has not been grafted.
Figure 5A:
FIG. 5a-d: Seedlings with primary and secondary lateral branch development from a cross between parents expressing free-branching phenotype. Developing secondary lateral branches circled in blue.
Figure 5B:
Figure 5C:
Figure 5D:

However, other horticultural elite characteristics, such as stem size and strength and bloom or bract size are also used as secondary selection criteria. By crossing selected free-branching seedlings with other poinsettias to develop other horticultural important trait, free-branching commercial cultivars can be developed. After selective breeding, the resulting plants, depicted for example in FIG. 2, produce numerous, large lateral branches.

Following selective breeding, such as detailed above the resulting poinsettia plants display attributes that were previously only achievable by pinching and/or phytoplasma infection. The plants produced numerous, large, lateral branches including branches within 7 nodes of the primary shoot meristem. The lateral branching occurred at up to 95%-100% of nodes prior to termination of vegetative growth of the primary shoot, therefore resulting in mature plants with a commercially desirable bushy habit. Moreover, these plants were able to pass the lateral branching trait onto progeny plants even when crossed with plants that did not comprise a lateral branching trait. Importantly, progeny of such a cross were able to inherit both the lateral branching trait and other horticultural elite traits from the second parent plant. Thus, the resulting plants exhibit bushy habit due to the high level of lateral branching (see, e.g., FIG. 2) and can also be bred to provide any additional elite trait that may be desired. This aspect is crucial in the case of commercial poinsettia plants because the market demands a wide variety of plants that display various bract and leaf colors and a range of sizes.

Without being bound by theory, the heritable lateral branching trait described here is believed to be controlled by multiple genetic loci. Because of the extremely complex pattern of inheritance it was not previously recognized that genetic elements could be combined to produce poinsettias with a lateral branching trait. Instead, it was believed that external manipulation by pinching and/or phytoplasma inoculation was required to produce commercially relevant amounts of branching. Even more surprisingly, it has now been found that, through successive breeding and selection, the disparate genetic elements contributing to the lateral branching trait can be combined in a plant that is also able to inherit and express other horticultural elite traits. This aspect is both crucial and unexpected because a priori it would have been expected that undesirable traits would be linked to one or more genetic elements contributing to lateral branching and that the resulting linkage drag have produced in plants that had no commercial viability. In contrast the plants described here display both and high level of branching and the horticultural elite phenotypes that are required by the commercial market.

The new plants provided herein produce numerous lateral shoots without the need for pinching or exogenous branching agents. These free branching plants are able to transmit the lateral branching trait to progeny not only by vegetative propagation, but also by sexual crossing with plants that do not a comprise a lateral branching trait. At least a portion of progeny plants from a sexual cross will comprise the lateral branching trait. Thus, the new free branching plants allow the lateral branching trait to be introgressed into poinsettias plants that have various horticultural desirable traits (e.g., brilliant bract color, large bracts or dark leaf color). Likewise, cuttings from free branching poinsettias plants can be used to produce commercial quantities of poinsettia plants without the need for pinching or grafting. This can substantially reduce the required labor and production costs for plant production. Accordingly, poinsettias comprising a lateral branching trait can be produced which comprise any combination for desired traits, such as specific bract colors (e.g., peppermint, red, marble, pink, white, red and pink bicolor (see, U.S. Plant Patent 8,771), salmon, purple, maroon, pink and cream bicolor, peach), size, uniform (e.g., rounded and mounded) plant habit, number or size of inflorescences and/or the number of bracts per inflorescence (e.g., 10-30 bracts per inflorescence).

Figure 7:
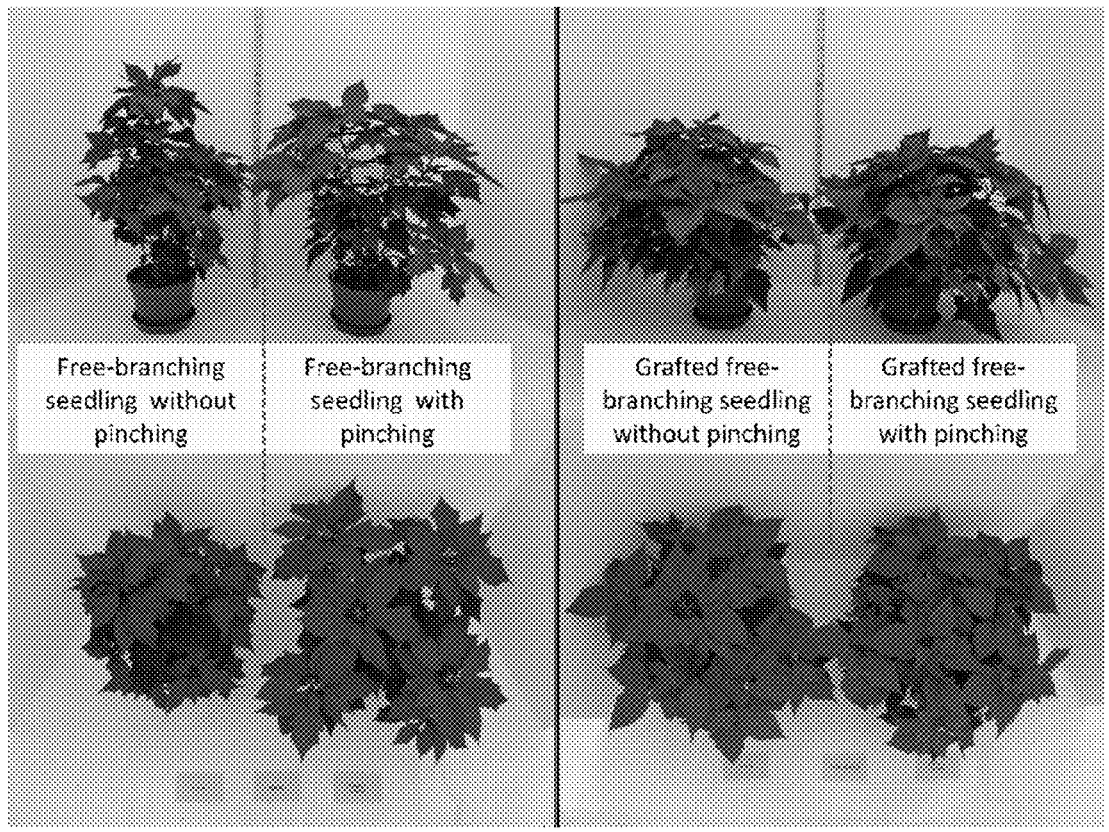
FIG. 7: Free-branching seedlings of the invention continue to express free-branching phenotype but presentation can be altered with grafting and/or pinching

Free-branching seedlings of plants of the invention can be grafted to introduce a branching agent and/or can be pinched, see e.g. U.S. Pat. No. 4,724,276 A incorporated herein by reference. These free-branching seedlings will continue to express free-branching phenotype. The effects of grafting and/or pinching are similar to their effect on poinsettias that are not genetically free-branching (FIG. 7).

Example plants comprising horticultural desirable traits that could be bred according to the embodiments include, but are not limited to those described in a U.S. Plant Patent Nos. 7,308, 7,825, 8,259, 8,771, 8,772, 8,773, 8,817, 8,833, 9,336, 9,632, 9,685, 9.8787, 9,879, 9,887, 10,183, 10,572, 10,603, 11,100, 11,124, 11,200, 11,403, 11,870, 11,889, 12,546, 12,604, 12,725, 12,770, 12,779, 12,782, 12,846, 12,849, 13,297, 13,312, 13,316, 13,326, 13,335 and/or 13,341, each incorporated herein by reference. Likewise, in some aspects, the lateral branching trait could be introgressed into any desired genetic background, such as into the genome of one of the plants provided in the aforementioned U.S. patents.

I. Definitions

Branching agent—As used herein the term "branching agent" refers to an exogenous agent that is provided to a poinsettias plant to stimulate lateral branching. For example, a branching agent could be an endophyte (e.g., a phytoplasma) or plant virus that is inoculated into plants or provided via a graft. Other branching agents include transgenes that are added to a poinsettia plant by transformation or introgression. Likewise a branching agent can be a plant hormone or a chemical agent such as cyclanilide. In certain aspects, a free branching poinsettia plant according to the embodiments is defined not having been treated with one or more branching agent or as not having been treated with any branching agent.

Free of phytoplasma infection—The plant has not been grafted with phytoplasma infected poinsettia or otherwise infected or inoculated with phytoplasma.

Free branching poinsettia—A poinsettia plant which comprises a plurality of lateral branches.

Main stem—the primary plant stem

Primary shoot meristem—The meristem tissue wherefrom vegetative growth occur at the top.

Node—the point at the stem where a leaf is attached.

Horticultural elite—Plants exhibiting desired horticultural traits are considered to be horticultural elite, viz. genetic traits. Traits that may be considered to confer elitism good longevity, large blooms and/or bracts, brilliant bract color, tolerance to pests, tolerance to disease, long flowering time, and the like.

Genetic transformation—A process of introducing a DNA molecules (e.g., a vector or expression cassette) into a cell or protoplast in which that exogenous DNA is incorporated into a chromosome or is capable of autonomous replication.

Introgression—The process of transferring a genetic trait (e.g., lateral branching) from one genotype to another.

Lateral branching trait—A trait which confers at least a first branch that extends from the primary shoot within 7 nodes of the primary shoot meristem before termination (e.g., flowering or pinching of the stem) of the primary shoot. A lateral branching trait as defined herein does not require pinching or phytoplasma infection for lateral branch formation. Such a lateral branching trait can also be defined by its ability to be passed on to at least a portion of progeny plants when a parent plant comprising the lateral branching trait is crossed with a second plant that does not comprise a lateral branching trait.

Pinching—As used herein the term "pinching" refers to removal of the growing tip, or terminal of a plant. Removal of the tip encourages development of lateral (side) shoots. Pinching can be done by hand using a knife or fingers to "snap" the tip from the plants or can be completed by a mechanical device.

Progeny—Any subsequent generation, including the seeds and plants there from which is derived from a particular parental plant or set of parental plants.

Regeneration—The process of growing a plant from a plant cell (e.g., plant protoplast, callus or explant) or a plant cutting.

Transgene—A DNA which has been incorporated into a host plant genome or is capable of autonomous replication in a host plant cell and is capable of causing the expression of one or more cellular products. Exemplary transgenes will provide the host cell, or plants regenerated there from, with a novel phenotype relative to the corresponding non-transformed cell or plant. Transgenes may be directly introduced into a plant by genetic transformation, or may be inherited from a plant of any previous generation which was transformed with the DNA.

Transgenic plant—A plant or progeny plant of any subsequent generation derived there from, wherein the DNA of the plant or progeny thereof contains an introduced exogenous DNA segment not originally present in a non-transgenic plant of the same strain. The transgenic plant may additionally contain sequences which are native to the plant being transformed, but wherein the "exogenous" gene has been altered in order to alter the level or pattern of expression of the gene.

II. Deposit Information

A representative deposit of 2500 seeds from free branching poinsettia plants, and from which free branching poinsettia plants comprising the lateral branching trait can be obtained, have been made with the National Collections of Industrial, Food and Marine Bacteria (NCIMB), 23 St. Machar Drive, Aberdeen AB2 1RY, Scotland, United Kingdom on Jun. 8, 2011. Those deposited seeds have been assigned Accession No. NCIMB 41844.

The foregoing deposits were made in accordance with the terms and provisions of the Budapest Treaty relating to deposit of microorganisms and were made for a term of at least thirty (30) years and at least five (05) years after the most recent request for the furnishing of a sample of the deposits is received by the depository, or for the effective term of the patent, whichever is longer, and will be replaced if it becomes non-viable during that period.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Breeding of Poinsettia Plants Comprising a Lateral Branching Trait

Poinsettia seedling 98-5594 was selected from a population of seedlings because it had a few lateral branches, although they only developed at the time of flowering. These plants were confirmed to phytoplasma-free. The 98-5594 seedling was used as the male parent and crossed to another seedling, which comprised desirable horticultural traits. The progeny from this cross expressed some lateral branch development. A seedling, 99-4637, was selected from the cross for the presence of lateral branching and was used as a female parent and crossed to a V-27 plant, which also expressed minimal lateral branching.

Again, a seedling was selected from the progeny based on the presence of lateral branching. The selected seedling, Z-98, was crossed to a commercial variety Celebrate 2 which comprises horticultural elite traits. Some but not all of the progeny from this cross expressed lateral branching. A seedling, PE3-57, was selected because it had large bracts and many of the lateral nodes had some developing shoot. PE3-57 was crossed to another seedling X-6 which comprised horticultural desirable traits, such as dark red bracts and compact stature, but did not express lateral branch development. In this cross 21% of the progeny expressed lateral branch development.

A seedling from the cross, PE6-26, was selected because it displayed branches developed from 95% of its nodes without pinching. All crosses with PE6-26 have yielded populations of progeny which contain seedlings that express lateral branches. Importantly progeny of PE6-26 are also able to inherit horticultural elite traits from parent plants and thus serve as a basis for production of commercial free branching poinsettia plants.

TABLE 1

Example crosses with free branching poinsettia lines.

| Female Parent | Male Parent | Comments |
| --- | --- | --- |
| PE7-63 | X 1280 (PE6-27) | 13(39%) show kindle development, 2w/breaker. By 12/7 73% w/ kindles. 7 Lt leaf: 26 Dark leaf. All Red-generally dark red. mid season. Few to moderate number of kindles per stem. |
| PE7-56 | X 1280 (PE6-27) | 6(40%) show kindle development, 4 w/breaker color. 8 Lt leaf: dark leaf. 1 pink: 6 Lt Red (Rose): 8 Red. |
| PE7-41 | X 1280 (PE6-27) | 1(3%) show kindle development. 20 Lt leaf: 4 dark leaf. Generally good vigour good bloom size. 1 Lt Red (Rose): 23 Bright Red. All Red. |
| PE4-33 | X 04-188-4 | 43% have kindles developing but elongation poor, development generally at base of plant, 16 Lt leaf: 54 Dk leaf. All red. Generally compact to moderately compact, variable timing, good centres, but may w/ helicopter bracts. |
| 1156 (PE3-20) | X PE6-25-B | 42% show slight kindle development. All Red. All dark leaf except for 7 minis. Generally moderately vigorous, good bract sizes, mid season, poor kindle development, many w/ white edge. |
| 1195 (PE4-22) | X PE4-32 | 54% show kindles; but poor kindle development. Generally mid to late season, medium size blooms, good centres variable ht, |

TABLE 1-continued

Example crosses with free branching poinsettia lines.

| Female Parent | Male Parent | Comments |
|---|---|---|
| 1156 (PE3-20) | X PE4-33 | 7 lt leaf: 47. All Red. 23% show kindles. Generally moderately vigorous, mid to late season, 12 lt leaf: 58 dark leaf, All Red. |
| PE4-33 | X PE5-51 | 74% show kindles. Generally late blooming, tall, vigorous, centres tend to be open, variable bloom size. 32 Lt leaf: 25 Dk leaf. |
| 1178 (PE3-71) | X 1084) (Z-85 | 37% with some kindles. Generally large blooms, centres ok. 31 Lt leaf: 33 Dk leaf. 28 white: 36 Red. |

REFERENCES

The following references, to the extent that they provide exemplary procedural or other details supplementary to those set forth herein, are specifically incorporated herein by reference.

U.S. Pat. No. 7,695,901.
U.S. Pat. Publ. Nos. 20070067876, and 20100281568.
U.S. Plant Patent Nos. 7,308, 7,825, 8,259, 8,771, 8,772, 8,773, 8,817, 8,833, 9,336, 9,632, 9,685, 9.8787, 9,879, 9,887, 10,183, 10,572, 10,603, 11,100, 11,124, 11,200, 11,403, 11,870, 11,889, 12,546, 12,604, 12,725, 12,770, 12,779, 12,782, 12,846, 12,849, 13,297, 13,312, 13,316, 13,326, 13,335 and 13,341.
Lee et al., *Int. J. Syst. Bact.*, 48:1153-1169, 1998.

The invention claimed is:

1. A free branching poinsettia plant comprising a lateral branching trait wherein the plant is free of phytoplasma infection and any other branching agent, wherein the poinsettia plant is obtained by introgression of the lateral branching trait from a plant grown from the seed deposited at NCIMB under the accession no. NCIMB 41844, said plant having been selected for lateral branching.

2. The poinsettia plant of claim 1, wherein the plant comprises 20 to 25 first branches.

3. The poinsettia plant of claim 1, wherein said lateral branching trait confers at least one first branch and at least one second branch that extends from one of said at least one first branch.

4. The poinsettia plant of claim 3, wherein said lateral branching trait confers one or more further branch(es), which extends from one of said one or more second branch or from another of said at least one further branch.

5. The poinsettia plant of claim 1, further comprising at least one horticultural elite trait.

6. The poinsettia plant according to claim 5, wherein said horticultural elite trait is selected from the group consisting of short stature, upright growth, strong branches, large blooms, large bracts, large inflorescences, vigorous growth, disease resistance, insect resistance, herbicide tolerance, increased longevity, midseason flowering, increased period of flowering, uniform plant habit, a desired leaf color or morphology, flower bracts with desirable colors and brilliant bract color.

7. A tissue culture of regenerable cells of the poinsettia plant of claim 1, wherein said tissue culture of regenerable cells comprises said lateral branching trait.

8. A method of producing a free branching poinsettia plant comprising crossing a plant of claim 1 with a second poinsettia plant and selecting a progeny plant comprising the lateral branching trait.

9. A method for obtaining a the poinsettia plant according to claim 1 comprising the step of introgression of the lateral branching trait from a plant grown from the seed deposited at NCIMB under the accession no. NCIMB 41844.

* * * * *